United States Patent [19]

Sommer et al.

[11] Patent Number: 4,677,204

[45] Date of Patent: Jun. 30, 1987

[54] CHEMICAL AGENTS

[75] Inventors: Harold Z. Sommer, Havre De Grace, Md.; John Krenzer, Oak Park, Ill.; Omer O. Owens, Abingdon; Jacob I. Miller, Baltimore, both of Md.

[73] Assignee: The United States of America as represented by the Secretary of the Army, Washington, D.C.

[21] Appl. No.: 512,246

[22] Filed: Dec. 7, 1965

[51] Int. Cl.[4] .......... C07D 213/62

[52] U.S. Cl. .......... 546/261

[58] Field of Search .......... 167/47; 260/296; 546/261

[56] References Cited

U.S. PATENT DOCUMENTS 3,137,702 6/1964 Luttringhaus et al. .......... 260/296

*Primary Examiner*—John F. Terapane

*Assistant Examiner*—John S. Maples

*Attorney, Agent, or Firm*—Anthony T. Lane; Robert P. Gibson; Harold H. Card, Jr.

EXEMPLARY CLAIM

1. A chemical toxic agent selected from the group consisting of:

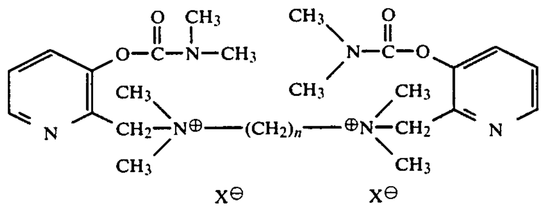

where n is an integer from 3 to 11 and X represents one equivalent of an anion.

11 Claims, No Drawings

CHEMICAL AGENTS

This invention relates to a series of new compounds that are extremely useful as chemical warfare agents.

The agents act mostly on the peripheral autonomic cholinergic nervous system. They interfere with the normal process of neuromuscular impulses from nerve to muscle. These compounds are extremely toxic at relatively low dose levels in various animals.

The object of this invention is to synthesize new lethal agents in high yield, wherein said products are well suited for industrial scale manufacture by means of a very simple procedure.

Other objects of and uses for the invention will in part be obvious and will in part appear hereinafter in the following detailed description thereof.

We have found that numerous compounds hereinafter set forth are effective toxic chemical agents. Advantageously, the agents are soluble in water, methanol and ethanol without any detrimental effects to said agent. Moreover, these agents are made by two distinct and economical methods.

In accordance with the invention, a solution of 2-dimethylaminomethyl-3-dimethylcarbamoxypyridine is allowed to react with an α,ω-dihalo-alkane, wherein the alkane radical has 3 to 11 carbon atoms, in the presence of sodium iodide and acetonitrile. The reaction is allowed to proceed for a period of six days at room temperature with formation of a crystalline material. This crystalline material is removed by filtration and triturated with acetone. The crude product is dissolved in hot ethanol and treated with charcoal. After the addition of ethyl acetate to the filtered solution, a crystalline product is formed, collected and dried.

A second method employed in this invention consists of reacting an α,ω-dihalo-alkane wherein the alkane radical consists of 3 to 11 carbon atoms, with 2-dimethylaminomethyl-3-dimethylcarbamoxypyridine in the presence of acetonitrile. This solution is heated on a steam bath for 6 hours and allowed to cool overnight at ambient temperature. The solution is filtered and the collected crystalline product is triturated with acetone. The product is dissolved in hot ethanol and treated with charcoal. Ethyl acetate is added to the filtered solution whereby a crystalline product is formed, collected and dried.

These compounds can be shown generically as follows:

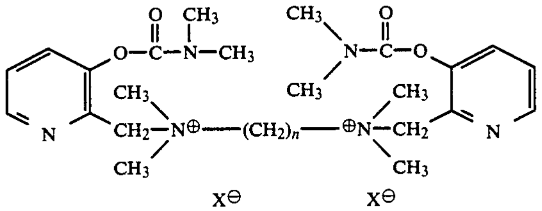

Where n is an integer from 3 to 11 inclusive and where X is one equivalent of a monovalent or polyvalent anion.

The procedure used for the preparation of the new toxic materials is schematically shown as follows:

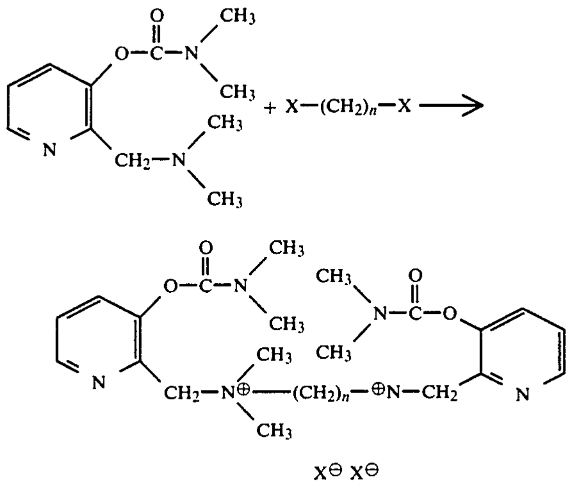

Where n is the same as above, X is a halide radical and $X^-$ is the corresponding halide anion, preferably chlorine or bromine.

In the above reaction, we have found that the incoming dihaloalkane adds to the nitrogen atom of the 2-dimethylaminomethyl moiety to the exclusion of the other nitrogen atoms because of the more basic nature of the former. If compounds are desired in which X is other than a halide ion, the above quaternary compounds are reacted with the desired acid by a simple exchange reaction as set forth below.

METHOD A

A solution of approximately 2 moles of 2-dimethylaminomethyl-3-dimethylcarbamoxypyridine, approximately one mole of α,ω-dihaloalkane, and a catalytic amount of sodium iodide in acetonitrile is allowed to stand at room temperature for six days. The crystalline material that is usually formed during the reaction period is removed by filtration and triturated with acetone. In the event no solid separates, ethyl acetate is added to precipitate the crude product, which is then dissolved in hot ethanol and treated with charcoal. Ethyl acetate is added to the filtered solution to precipitate the crystalline product, which is collected and dried.

METHOD B

A solution of approximately 2 moles of 2-dimethylaminomethyl-3-dimethylcarbamoxypyridine and approximately one mole of α,ω-dihaloalkane in acetonitrile is heated on a steam bath for 6 hours and allowed to stand overnight at room temperature. The crystalline product is collected by filtration and triturated with acetone. In the event no solid separates, ethyl acetate is added to precipitate the crude product, which is then dissolved in hot ethanol and treated with charcoal. Ethyl acetate is added to the filtered solution to precipitate the crystalline product, which is collected and dried.

The compounds that are representative of our invention are listed below by code number, name, and chemical structure.

EA 4048 1,3-Bis[Methyl-2-(3-dimethylcarbamoxypyridyl) methylamino]propane dimethobromide -continued

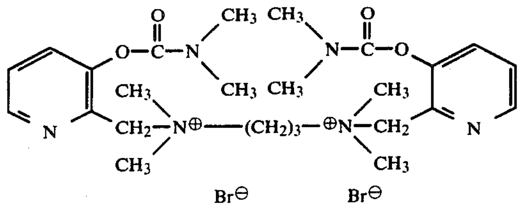

EA 4038 1,4-Bis[Methyl-2-(3-dimethylcarbamoxypyridyl) methylamino]butane dimethobromide

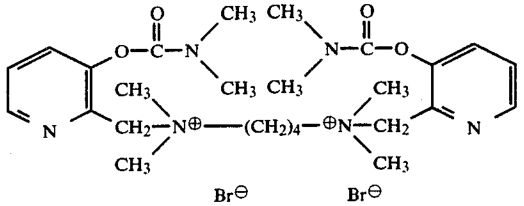

EA 4026 1,5-Bis[Methyl-2-(3-dimethylcarbamoxypyridyl) methylamino]pentane dimethobromide

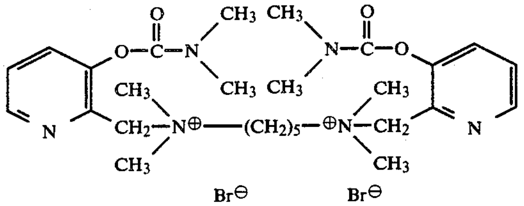

EA 3948 1,6-Bis[Methyl-2-(3-dimethylcarbamoxypyridyl) methylamino]hexane dimethobromide

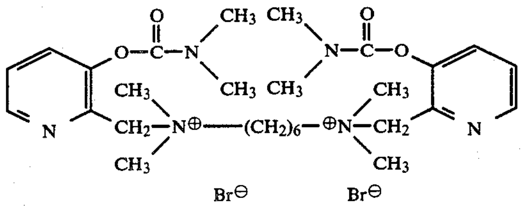

EA 4181 1,7-Bis[Methyl-2-(3-dimethylcarbamoxypyridyl) methylamino]heptane dimethobromide

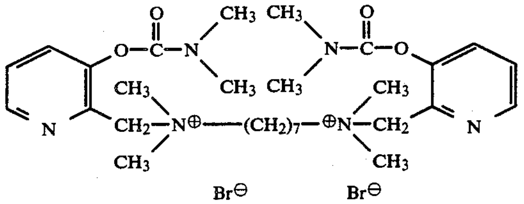

EA 3990 1,8-Bis[Methyl-2-(3-dimethylcarbamoxypyridyl) methylamino]octane dimethobromide

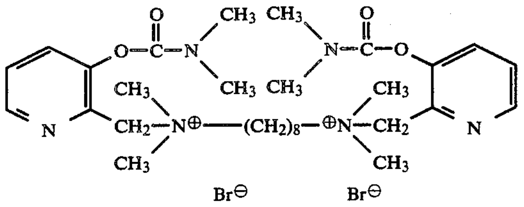

EA 4056 1,9-Bis[Methyl-2-(3-dimethylcarbamoxypyridyl) methylamino]nonane dimethobromide -continued

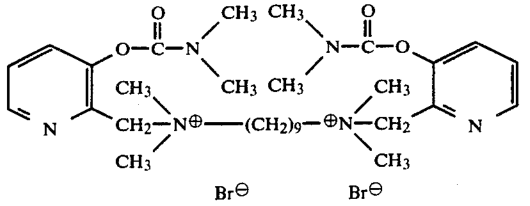

EA 3887 1,10-Bis[Methyl-2-(3-dimethylcarbamoxypyridyl) methylamino]decane dimethobromide

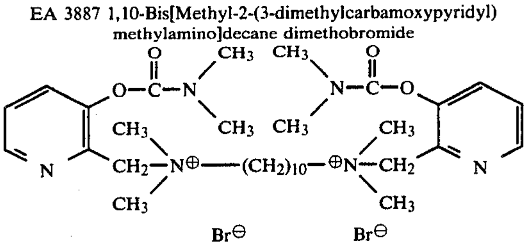

EA 3887A 1,10-Bis[Methyl-2-(3-dimethylcarbamoxypyridyl) methylamino]decane dimethoiodide

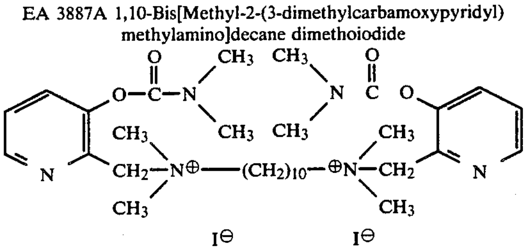

EA 4057 1,11-Bis[Methyl-2-(3-dimethylcarbamoxypyridyl) methylamino]undecane dimethobromide

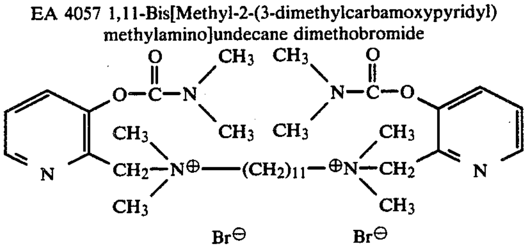

We have shown preferred compounds in which the anion is limited to the halogen moiety, in particular the bromides, since the dibromoalkanes are readily available and are good quaternizing agents. In general, however, it is only necessary that the anions merely have to meet the requirement of being capable of forming a stable salt with the quaternary nitrogens. Thus, the halogen ion can be exchanged with other anions of a relatively strong monovalent or polyvalent acids by conventional methods. For example, if X is a bromide in the bis-quaternary compound, it can be treated with a basic ion exchange resin or mixed with silver oxide and subsequently the desired acid is added. In like manner the sulfate, nitrate, hydrogen, oxalate, perchlorate salts may be prepared. Representative examples of these additional monovalent or polyvalent bis quaternary compounds are:

1,8-bis[methyl-2-(3-dimethylcarbamoxypyridyl)methylamino]octane sulfate 1,8-bis[methyl-2-(3-dimethylcarbamoxypyridyl)methylamino]octane dinitrate 1,9-bis[methyl-2-(3-dimethylcarbamoxypyridyl)methylamino]nonane dihydrogenoxalate 1,9-bis[methyl-2-(3-dimethylcarbamoxypyridyl)methylamino]nonane diperchlorate The examples shown in Table I are also illustrative of our invention but it is to be understood that the invention is not to be limited thereto since the scope of the appended claims defines our invention.

TABLE I

| Ex. | EA No. | Method of Preparation | Melting Point °C. | Yield | Soluble in | Analysis Calculated % C | H | O | Br | I | Found % C | H | O | Br | I | Toxicities IV $LD_{50}$ (mg/kg) Mice | Rabbits |
|---|---|---|---|---|---|---|---|---|---|---|---|---|---|---|---|---|---|
| 1 | 4048 | B | 198–199 | 42[a] | Water Methanol Ethanol | 45.1 | 6.3 | 12.0 | | | 45.2 | 6.3 | 11.7 | | | >32 | >20 |
| 2 | 4038 | B | 170–175 | 36[b] | Water Methanol Ethanol | 44.7 | 6.6 | 13.7 | | | 45.0 | 6.7 | 13.3 | | | 3.2 | 5.6 |
| 3 | 4026 | B | 188–194 | 44[a] | Water Methanol Ethanol | 46.7 | 6.7 | | 23.0 | | 46.8 | 6.8 | | 23.0 | | 0.063 | 0.056 |
| 4 | 3948 | B | 145–147 | 67[a] | Water Methanol Ethanol | 47.6 | 6.8 | 11.3 | 22.6 | | 47.6 | 7.0 | 11.7 | 22.7 | | 0.0178 | 0.0176 |
| 5 | 4181 | A | 160–163 | 19 | Water Methanol Ethanol | 49.4 | 6.8 | | 22.7 | | 49.4 | 6.9 | | 22.6 | | 0.013 | 0.0056 |
| 6 | 3990 | A,B | 190–191 | 64 | Water Methanol Ethanol | 50.1 | 7.0 | | 22.2 | | 50.1 | 7.2 | | 22.3 | | 0.0063 | 0.0026 |
| 7 | 4056 | B | 100–105 | 95 | Water Methanol Ethanol | 50.8 | 7.1 | | 21.9 | | 50.6 | 7.0 | | 21.7 | | 0.011 | 0.0027 |
| 8 | 3887 | A,B | 198–199 | 73 | Water Methanol Ethanol | 51.5 | 7.3 | | 21.4 | | 51.4 | 7.2 | | 21.2 | | 0.010 | 0.0042 |
| 9 | 3887 A | B | 160–161 | 60 | Water Methanol Ethanol | 45.7 | 6.5 | | | 30.2 | 45.5 | 6.2 | | | 30.0 | 0.010 | 0.005 |
| 10 | 4057 | A | 130–132 | 62 | Water Methanol Ethanol | 52.1 | 7.4 | | 21.1 | | 52.5 | 7.4 | | 21.1 | | 0.009 | 0.005 |

N.B.
[a]Monohydrate
[b]Dihydrate
mg. = milligram
kg. = kilogram weight of the animal
$LD_{50}$ = the dosage required to kill 50% of the test animals.
IV = Intravenous

We claim:

1. A chemical toxic agent selected from the group consisting of:

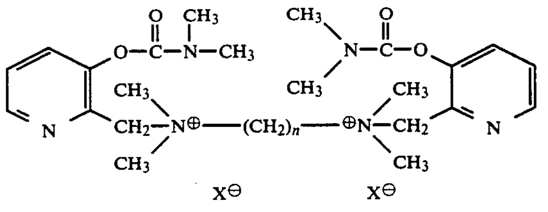

where n is an integer from 3 to 11 and X represents one equivalent of an anion.

2. The salts of claim 1 wherein X is selected from the group of anions consisting of halide, sulfate, oxalate, nitrate, and perchlorate.

3. The compound 1,3-bis[methyl-2-(3-dimethylcarbamoxypyridyl)methylamino]propane dimethobromide.

4. The compound 1,4-bis[methyl-2-(3-dimethylcarbamoxypyridyl)methylamino]butane dimethobromide.

5. The compound 1,5-bis[methyl-2-(3-dimethylcarbamoxypyridyl)methylamino]pentane dimethobromide.

6. The compound 1,6-bis[methyl-2-(3-dimethylcarbamoxypyridyl)methylamino]hexane dimethobromide.

7. The compound 1,7-bis[methyl-2-(3-dimethylcarbamoxypyridyl)methylamino]heptane dimethobromide.

8. The compound 1,8-bis[methyl-2-(3-dimethylcarbamoxypyridyl)methylamino]octane dimethobromide.

9. The compound 1,9-bis[methyl-2-(3-dimethylcarbamoxypyridyl)methylamino]nonane dimethobromide.

10. The compound 1,10-bis[methyl-2-(3-dimethylcarbamoxypyridyl)methylamino]decane dimethobromide.

11. The compound 1,11-bis[methyl-2-(3-dimethylcarbamoxypyridyl)methylamino]undecane dimethobromide.

* * * * *